United States Patent
Wells et al.

(10) Patent No.: US 7,867,371 B2
(45) Date of Patent: Jan. 11, 2011

(54) ELECTROCHEMICAL SENSOR AND METHOD OF MANUFACTURE

(75) Inventors: Steven Wells, Huntington Beach, CA (US); Gert Burkhardt, Pasadena, CA (US); Anthony Thai, Orange, CA (US)

(73) Assignee: Georg Fischer Signet, LLC, El Monte, CA (US)

( * ) Notice: Subject to any disclaimer, the term of this patent is extended or adjusted under 35 U.S.C. 154(b) by 1140 days.

(21) Appl. No.: 11/533,989

(22) Filed: Sep. 21, 2006

(65) Prior Publication Data

US 2008/0073210 A1    Mar. 27, 2008

(51) Int. Cl.
*G01N 27/30* (2006.01)
(52) U.S. Cl. .......... 204/435; 204/433; 204/409; 205/787.5; 324/438
(58) Field of Classification Search ......... 204/400–402, 204/409–420, 433, 435; 205/787.5, 789, 205/789.5, 793; 324/438
See application file for complete search history.

(56) References Cited

U.S. PATENT DOCUMENTS

| | | | |
|---|---|---|---|
| 4,112,352 A | 9/1978 | Barben | |
| 4,128,468 A | 12/1978 | Bukamier | |
| 4,235,688 A | 11/1980 | Sudrabin et al. | |
| 5,145,565 A | 9/1992 | Kater | |
| 5,147,524 A | 9/1992 | Broadley | |
| 5,152,882 A | 10/1992 | Benton | |
| 5,346,606 A | 9/1994 | Christner et al. | |
| 5,630,921 A * | 5/1997 | Hess et al. | 204/435 |
| 6,054,031 A | 4/2000 | Benton | |
| 6,416,653 B1 | 7/2002 | Barben, II et al. | |
| 6,423,197 B1 | 7/2002 | Lenferink et al. | |
| 2002/0043095 A1 | 4/2002 | Mason et al. | |
| 2004/0195098 A1 | 10/2004 | Broadley et al. | |

OTHER PUBLICATIONS

"pH Theory and Measurement", *Barben Analyzer Technology, LLC*, Carson City, NV., (early than Jun. 2006),pp. 1-11.
"Sensor Evolution", *Barben Analyzer Technology, LLC*, Carson City, NV, 5 pages, (Earlier than Jun. 2006), pp. 4-5.
Spiegler, K. S., "Determination of Resistance Factors of Porous Diaphragms and Electrodes", *Electrochemical Society*, vol. 113, No. 2, 0013-4651, (1966), pp. 161-165.

* cited by examiner

*Primary Examiner*—Nam X Nguyen
*Assistant Examiner*—Bach T Dinh
(74) *Attorney, Agent, or Firm*—Tsircou Law, P.C.

(57) ABSTRACT

An electrochemical sensor is provided that includes a housing defining a cavity for a reference electrolyte and defining an opening to the cavity configured to be proximate to a target fluid. The sensor further includes a junction plug comprising a porous material and a cross member impermeable to a target fluid positioned between the junction plug and the cavity. The cross member includes a planar portion disposed against the junction plug that defines an aperture to enable electrochemical communication between the target fluid and the reference electrolyte.

18 Claims, 5 Drawing Sheets

ELECTROCHEMICAL SENSOR AND METHOD OF MANUFACTURE

BACKGROUND OF THE INVENTION

The present invention relates generally to electrochemical sensors and, more particularly, to such sensors having a reference electrode and a measuring electrode for measuring parameters of a target fluid.

Electrochemical sensors have long been used to measure properties of fluids. Such sensors typically include a measuring electrode assembly and a reference electrode assembly, both which are electrically coupled to an instrument that senses the difference in electrical potential between the electrodes. In sensors of this kind, the measuring electrode assembly typically is exposed directly to the target fluid; whereas the reference electrode assembly is immersed in a stable electrolytic solution, i.e., a reference electrolyte. Sensors of this kind further include an ion-permeable separator, commonly referred to as liquid junction or salt bridge, disposed between the reference electrolyte and the target fluid, to enable a closed circuit between the electrodes.

In use, the measuring electrode generates a potential that varies as a function of prescribed parameters of the target fluid. The potential difference between the measuring electrode and the reference electrode provides a basis for measuring the prescribed parameters of the target fluid. For a precise reading, the reference electrode must provide a stable potential.

The liquid junction plays an important role in achieving and maintaining a stable potential for the reference electrode. Ideally, the liquid junction should enable ionic communication between the reference electrolyte and the target fluid, while otherwise preventing transfer or intermingling of the fluids. Contamination or dilution of the reference electrolyte can unduly inhibit performance of the reference electrode. Moreover, contamination or reaction with the reference electrode or electrolyte is of particular concern when used in harsh chemical environments. The ability of the liquid junction to inhibit diffusion of the measured fluid, and ions therefrom, can be generally referred to as its resistance factor.

Much attention has been given to designing effective liquid junctions having a high resistance factor. Many approaches attempt to establish a tortuous path for ions through the junction by confining travel through relatively complex structural configurations that incorporate multiple components assembled together. For example, certain approaches include multiple layers held together with wood dowels. Although generally effective, such approaches are relatively expensive and time-consuming to manufacture. Moreover, performance of such approaches can deteriorate with time.

It should be appreciated that there remains a need for an electrochemical sensor that addresses these concerns. The present invention fulfills this need and others.

SUMMARY OF THE INVENTION

In general terms, the present invention provides an electrochemical sensor comprising a housing defining a cavity for a reference electrolyte and defining an opening to the cavity configured to be proximate to a target fluid. The sensor further includes a junction plug comprising a porous material and a cross member impermeable to a target fluid positioned between the junction plug and the cavity. The cross member includes a planar portion disposed against the junction plug that defines an aperture to enable electrochemical communication between the target fluid and the reference electrolyte. Thus, ionic exchange must pass through the aperture, thereby enhancing the resistance factor of the sensor assembly.

More specifically, and by way of example, the electrochemical sensor comprises a housing having an outer member and an inner member disposed within the outer member. The inner member includes an axial bore configured to receive a measuring electrode. A junction plug of porous material positioned such that a first surface contacts the target fluid and a second surface is proximate to the cavity of the housing. The housing includes a cross member impermeable to the target fluid positioned between the junction plug and the cavity. The cross member defines an aperture in a single prescribed region of the cross member to enable electrochemical communication between the target fluid and the reference electrolyte.

In another embodiment of the invention, the electrochemical sensor includes a housing of unitary construction defining a cavity for a reference electrolyte and having a cross member between the cavity. The sensor further includes a junction plug having a first surface that contact a target fluid and a second surface that contacts the cross member.

In another embodiment, the housing includes an outer cylindrical member and an inner member disposed within the outer member. The outer member includes the cross member. Alternatively, the cross member can be provided as a separate component or even affixed to the junction plug. The cross member covers between about 50 percent to 95 percent of the second surface of the junction plug.

In a detailed aspect of an exemplary embodiment of the invention, the cross member includes a stepped portion and a planar portion disposed against the junction plug. The stepped portion and the junction plug define a void.

A method of manufacturing an electrochemical sensor is also provided. The method includes:

providing a housing defining a cavity for a reference electrolyte and defining an opening to the cavity configured to be proximate to a target fluid, the housing configured to couple to a measuring electrode;

disposing a reference electrode within the cavity of the housing and surrounded by the reference electrolyte; and disposing a junction plug comprising porous material at a distal end of the housing such that a first surface of the plug can contact the target fluid and a second surface is disposed within the housing proximate to the cavity of the housing; and providing a cross member formed of material impermeable to the target fluid, the cross member positioned between the junction plug and the cavity, the cross member including a planar portion disposed against the second surface of the junction plug, the planar portion of the cross member defining an aperture to enable electrochemical communication between the target fluid and the reference electrolyte.

For purposes of summarizing the invention and the advantages achieved over the prior art, certain advantages of the invention have been described herein. Of course, it is to be understood that not necessarily all such advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment disclosed.

BRIEF DESCRIPTION OF THE DRAWINGS

Embodiments of the present invention will now be described, by way of example only, with reference to the following drawings in which.

DETAILED DESCRIPTION OF THE PREFERRED EMBODIMENTS

Figure 1:
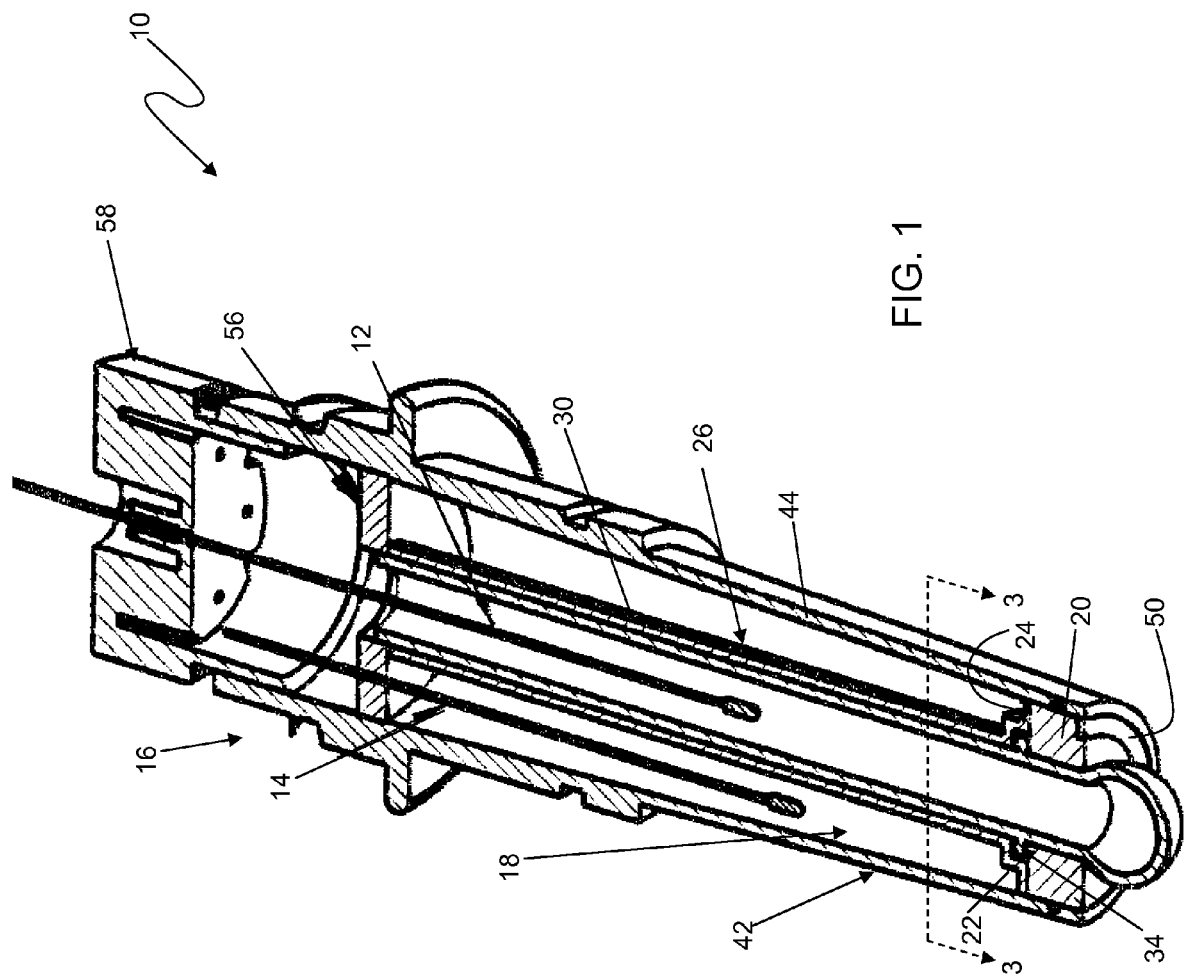
FIG. 1 is a cross-sectional view of a first embodiment of an electrochemical sensor in accordance with the present invention, depicting a reference electrode disposed within a cavity.
Figure 2:
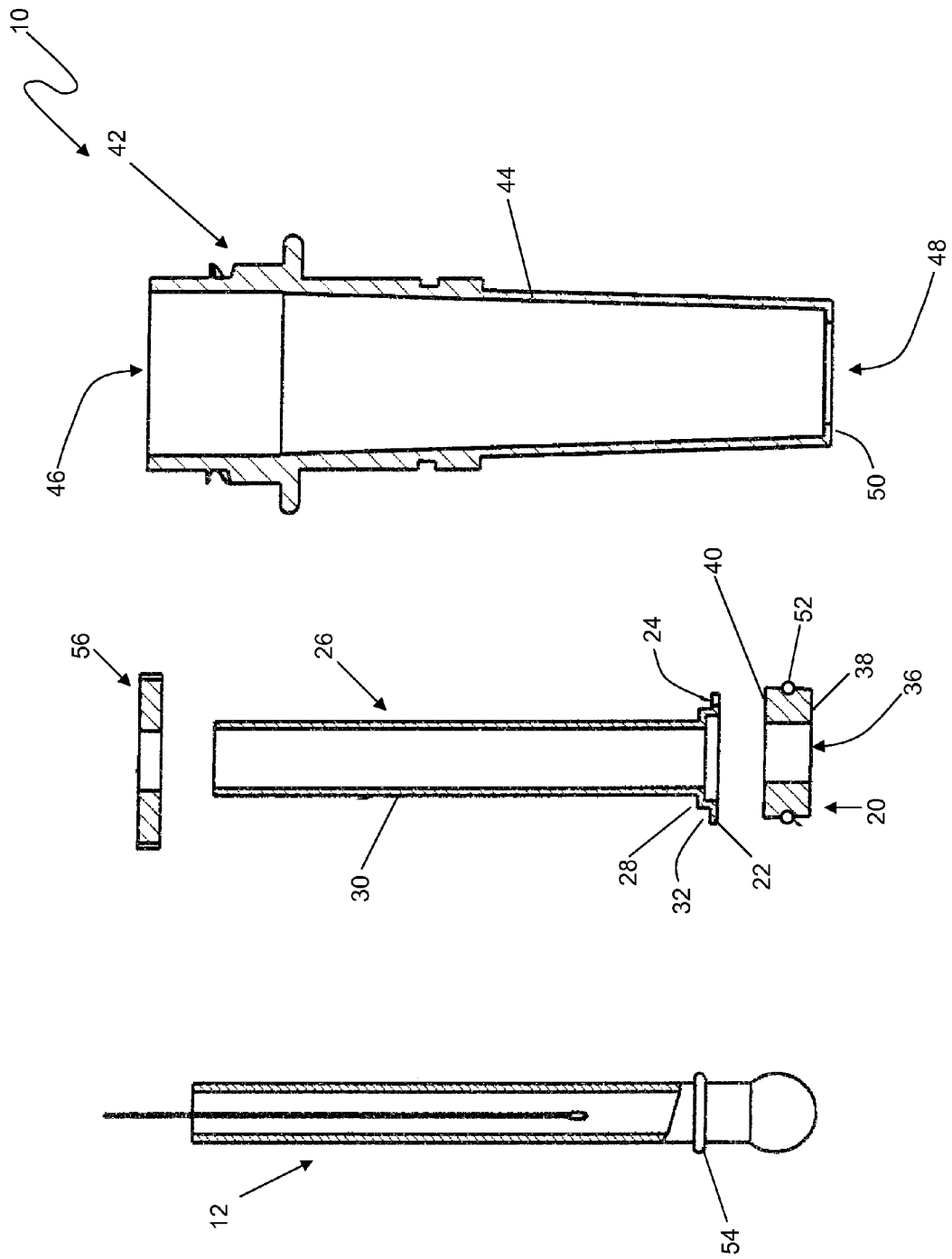
FIG. 2 is a partially exploded view of the electrochemical sensor of FIG. 1.

Referring now to the drawings, and particularly to FIGS. 1 and 2, there is shown an electrochemical sensor assembly 10, for measuring parameters of a target fluid (not shown), such as ORP or specific ions, e.g., pH or sodium. The sensor assembly 10 includes a measuring electrode 12 (e.g., glass pH electrode) and a reference electrode 14 coupled to a housing 16. The reference electrode is disposed within a cavity 18 of the housing and is surrounded by a reference electrolyte. The sensor assembly includes a liquid junction comprising a plug 20 disposed at distal end of the housing and further includes a cross member 22 disposed between the plug and the cavity. The cross member defines an aperture 24 that enables electrochemical communication between the target fluid and the reference electrolyte. Thus, ionic exchange must occur through the aperture, thereby enhancing the resistance factor of the sensor assembly.

The cross member 22 is formed of material impermeable to the target fluid. In the exemplary embodiment, the cross member is formed of molded plastic and is integrally formed with an inner member 26 of the housing 16. The aperture 24 is provided in a single prescribed region of the cross member. With the cross member in place, ions traveling between the target fluid and the reference electrolyte must migrate axially through and transverse across the junction plug 20 to pass through the aperture of the cross member, resulting in an increased effective path length through the junction plug.

The cross member 22 includes a stepped portion 28 disposed about a cylindrical bore 30 of the inner member and a planar portion 32 that extends from the stepped portion and positioned against the junction plug. The stepped portion and the junction plug define a void 34 about bore for receiving an o-ring 54 disposed about the measuring electrode.

In the exemplary embodiment, the junction plug 20 defines a central passage 36 that enables the measuring electrode 12 to extend beyond the liquid junction, to contact the target fluid. The junction plug includes a distal surface 38 that is exposed directly to the target fluid and a proximal surface 40 abutting the cross member 24.

The distal surface 38 of the junction plug 20 provides a relatively substantial surface area, to enabling effective exposure to the target fluid and minimizing clogging of the plug. The junction plug 20 is confined in an opening defined by the housing.

In the exemplary embodiment, the junction plug 20 is formed of a unitary construction of porous ultra-high molecular weight polyethylene. Nonetheless, other material having suitable characteristics can be used. For example, effective materials include ground glass, ceramic, other porous plastics, and wood. The liquid junction can be formed of multiple components and materials.

Figure 3:
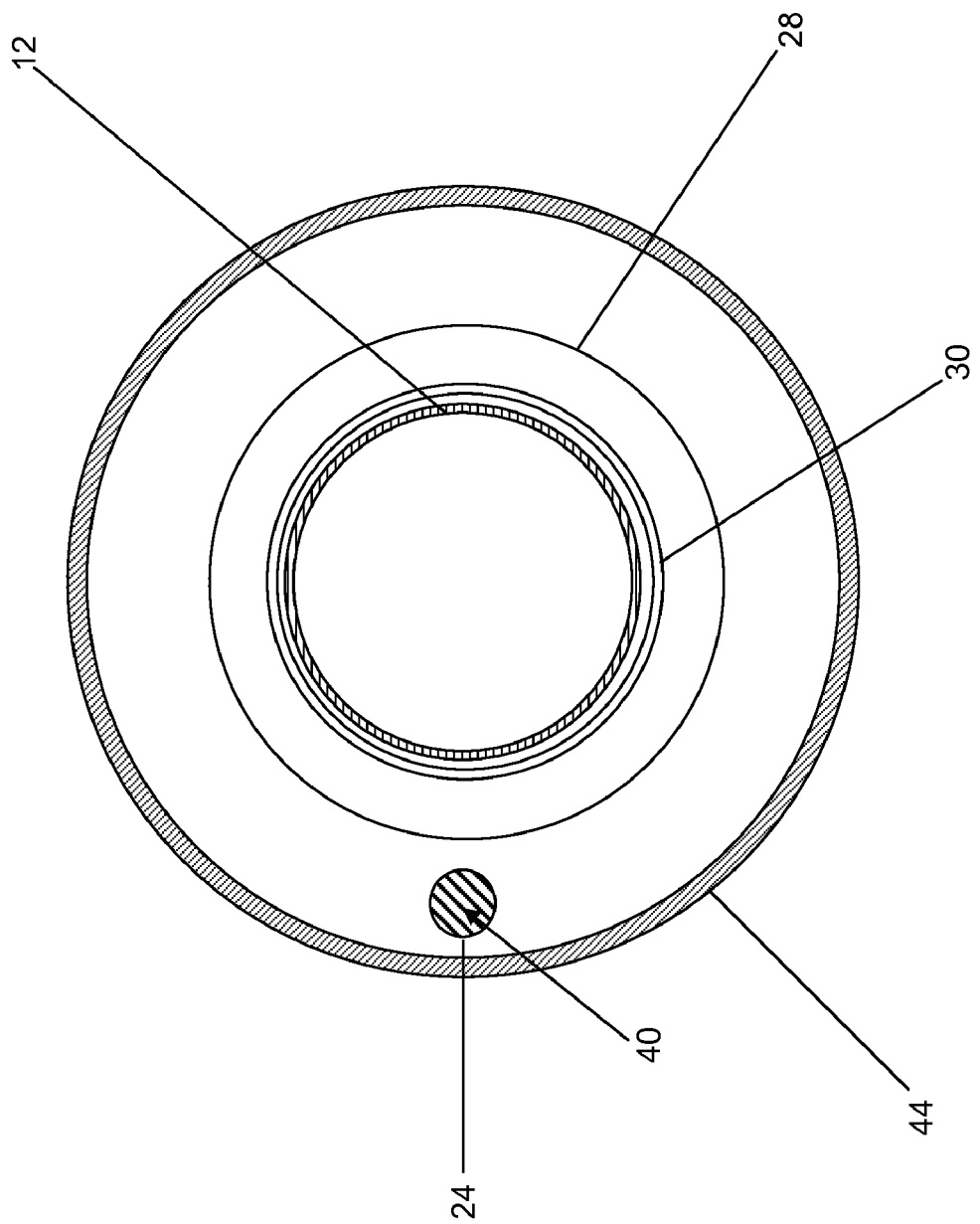
FIG. 3 is a cross-sectional view, taken along the line 3-3 of the electrochemical sensor of FIG. 1, depicting an aperture defined by the cross member of the housing assembly.

As best seen in FIG. 3, the cross member 22 effectively substantially covers the proximal surface 40 of the junction plug. Preferably, the cross member covers between about 50 percent to 98 percent of the proximal surface of the junction plug. In the exemplary embodiment, the cross member covers about 95 percent of the proximal surface. The aperture 24 is defined by the planar portion of the cross member. In the exemplary embodiment, the cross member defines a single circular aperture 24, however, other configurations can be used in other embodiments. For example, several apertures as well as other shapes, e.g., ring, rectangle, and so on, can be used. Moreover, in other embodiments, the cross member can be attached directly to the proximal surface of the cross member.

With reference to FIG. 2, the housing 16 includes the inner member 26 and an outer member 42. The outer member has a sidewall 44 and defines proximal and distal openings 46, 48, respectively. The outer member includes an inwardly facing flange 50 disposed about the distal opening. The flange is sized such that the junction plug 20 can be securely seated in place proximate to the distal opening to directly contact the target fluid. An o-ring 52 is disposed about the junction plug to engage the sidewall 44 of the outer member, providing a secure seal about the plug.

The inner member 26 of the housing 16 is coupled to and disposed within the outer member 42. The cylindrical bore 30 of the inner member is aligned with a longitudinal axis of the housing and configured to receive the measuring electrode 12. The sidewall 44 of the outer member is generally equidistantly spaced from the bore about the circumference thereof.

As previously mentioned, the inner member 26 provides the cross member 22. The cross member extends between the cylindrical bore and the sidewall 44 of the outer member. In the exemplary embodiment, the inner member is permanently affixed in place. The sidewall of the outer member slope inwardly from the proximal opening to the distal opening.

During assembly, the measuring electrode 12 is inserted into the plug 20. The o-ring is put down over the back of the measuring electrode 12, fitting snugly against the plug 20. The assembly is then inserted through the proximal opening 46. The inner member 26 is inserted into the outer member 42 through the proximal opening. The components are sized such that the diameter of the cross member 22 will correspond to the inner diameter of the outer member proximate to junction plug, once the plug is in place. In this manner, the cross member will directly contact the junction plug, as well as, the sidewall 44 of the outer member 42. Adhesive material can be provided, as needed. Nonetheless care should be taken to ensure that the aperture 24 does not become blocked with material that would bar electrochemical communication between the target fluid and the reference electrolyte.

In other embodiments, the inner member can be coupled to the outer cylindrical member in such manner to enable disassembly for maintenance purposes. For example, the inner and outer members can couple via cooperative attachments assemblies, e.g., threaded portions, tongue and groove engagements, and other suitable attachments.

In the exemplary embodiment, the outer and the inner members 26, 42, respectively, are formed of molded plastic, such as polypropylene, PP. In other embodiments, other materials can be used. Some examples of other material that can be used include polyphenylsulfone PPS, polyvinyl chloride PVC, chlorinated polyvinyl chloride CPVC, polyvinyldiflouride PVDF, or other materials known in the art having appropriate chemical resistivity for a particular application.

The sensor assembly 10 further includes an upper seal 56 positioned proximate to the proximal end of the outer member. The upper seal is configured to engage the cylindrical bore of the inner member and the sidewall 44 of the outer member 42 in such a manner as to aid in defining the reference cavity 18. The reference electrode is disposed within cavity, in this embodiment, opposite the aperture 24 of the cross member.

In the exemplary embodiment, a gelled reference electrolyte is used, such as, KCl saturated with AgCl acrylamide gel. Nonetheless, other reference electrolytes, including gels and liquids, can be selected as requirements dictate for particular uses.

The measuring electrode 12 and a reference electrode 14 are configured to be coupled to instrumentation, e.g., amplifier (not shown), to sense the potential of the measuring electrode and the reference electrode. The housing further includes a cap 58 received atop the proximal opening 46 of the outer member. Wires attached to the electrodes pass through the cap to couple to the instrumentation.

In the exemplary embodiment, a glass pH electrode is used. In use, the end portion of the measuring electrode 12 exposed to the target fluid such that the measuring electrode is electrochemically coupled to the target fluid. In the exemplary embodiment, a sensor assembly is configured to detect pH and ORP. However, other embodiments can configured to measure these or other parameters, individual or in combination. For example, other types of specific ions that can be measured include, for example, ammonium, bromide, chloride, fluoride, sulfide, nitrate, and sodium.

The reference electrode 14 is not directly exposed to the target fluid; rather it is surrounded by a reference electrolyte within a cavity 18 defined by the housing, enabling the reference electrode to provide a stable potential for comparison against the potential of the measuring electrode. In the exemplary embodiment, an Ag/AgCl type reference electrode is used, nonetheless, various other types of reference electrodes known in the art can be used.

Figure 4:
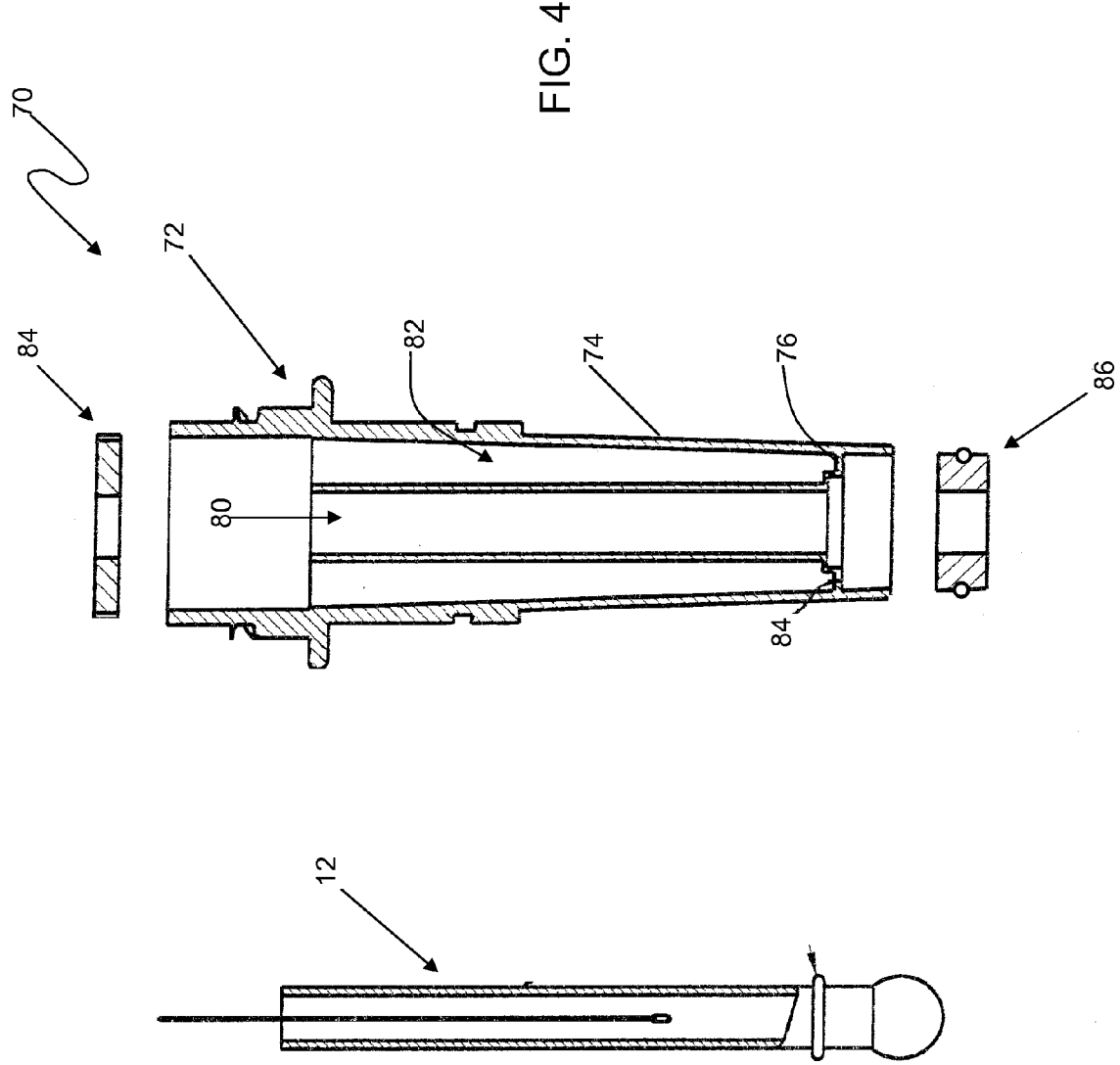
FIG. 4 is a partially exploded view of a second embodiment of an electrochemical sensor in accordance with the present invention, depicting a reference electrode disposed within a cavity.
Figure 5:
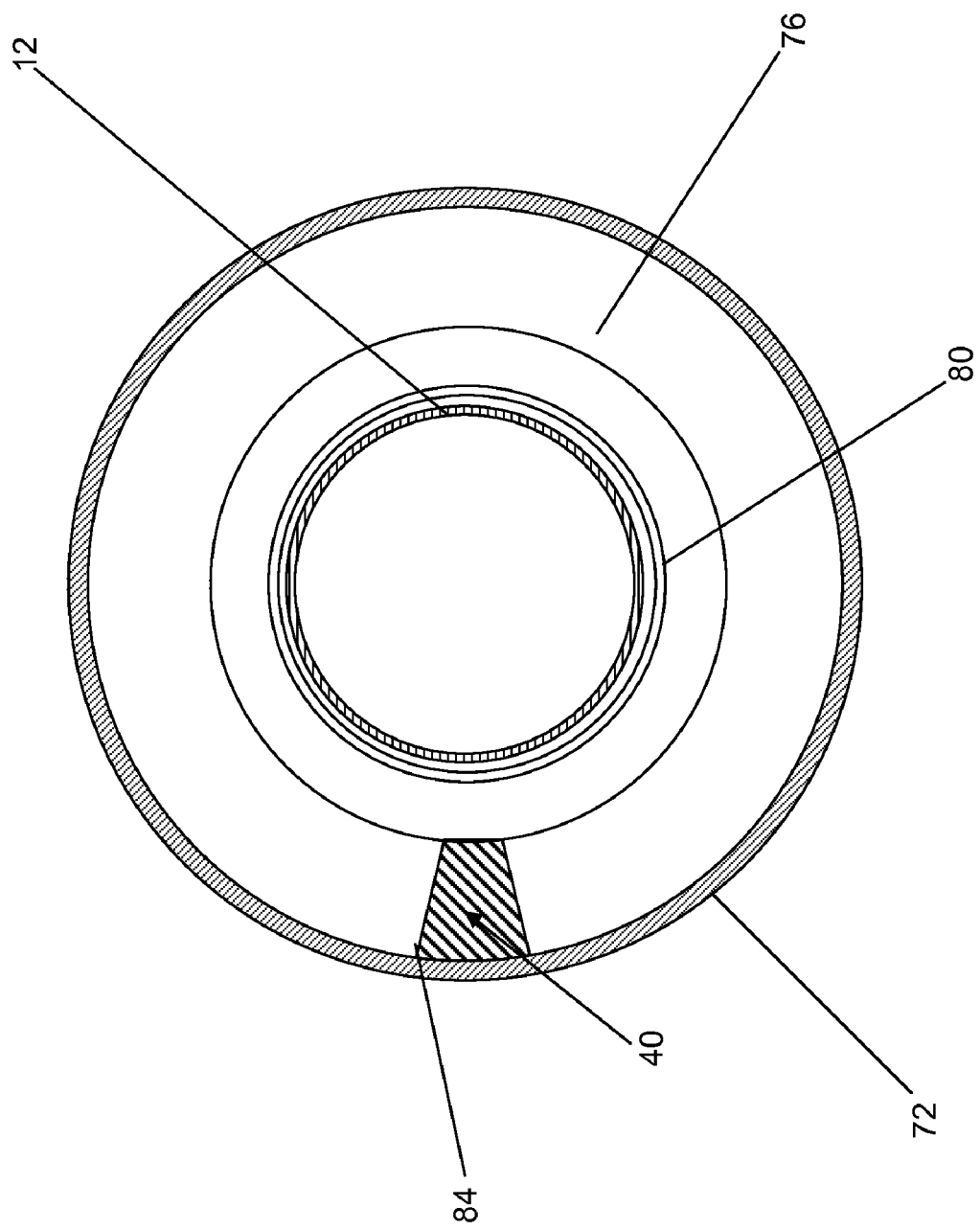
FIG. 5 is a cross-sectional view, similar to FIG. 3, of the electrochemical sensor of FIG. 4, depicting an aperture defined by the cross member of the housing assembly.

With reference now to FIGS. 4 and 5, a second embodiment of a sensor assembly 70 is provided, having a housing 72 formed of a unitary construction, e.g., molded plastic. Otherwise, the housing is similarly configured to the housing of the first embodiment, including a cylindrical sidewall 74 and a circular cross member 76 disposed proximate to a distal end 78 of the housing. The housing defines a central bore 80 for the measuring electrode 12 and a cavity 82 for containing the reference electrolyte. The cross member 76 defines an aperture 84 aligned with the cavity for the reference electrode. The cross member is disposed between the junction plug 86 and the cavity to enable electrochemical communication between the target fluid and the reference electrolyte. In this embodiment, the aperture is configured as a single radial segment confined in a prescribed region of the cross member.

It should be appreciated from the foregoing that the present invention provides an electrochemical sensor that includes a housing defining a cavity for a reference electrolyte and defining an opening to the cavity configured to be proximate to a target fluid. The sensor further includes a junction plug comprising a porous material and a cross member formed of material impermeable to a target fluid positioned between the junction plug and the cavity. The cross member includes a planar portion disposed against the junction plug that defines an aperture to enable electrochemical communication between the target fluid and the reference electrolyte. Thus, ionic exchange must pass through the aperture, thereby enhancing resistance factor of the sensor assembly.

Although the invention has been disclosed in detail with reference only to the exemplary embodiments, those skilled in the art will appreciate that various other embodiments can be provided without departing from the scope of the invention. Accordingly, the invention is defined only by the claims set forth below.

What is claimed is:

1. An electrochemical sensor, comprising:
   an elongated housing defining a longitudinal axis, the housing having a proximal end and a distal end configured to be exposed to a target fluid, the housing further defining a cavity substantially filled with a gelled or liquid reference electrolyte, the housing having an outer tubular wall formed of molded plastic, axially aligned with the longitudinal axis of the housing, the outer wall impermeable to the reference electrolyte and the target fluid,
   an inner tubular wall formed of molded plastic, disposed within the outer wall, and axially aligned with the longitudinal axis of the housing, the inner wall impermeable to the reference electrolyte and the target fluid, the inner wall defining an axial bore, and
   a cross member extending between the outer wall and the inner wall proximate the distal end of the housing, the cross member including a planar portion defining an aperture to enable electrochemical communication between the target fluid and the reference electrolyte within the cavity, wherein the cavity is bounded by the outer wall, the inner wall and the cross member;
   the cross member of the housing is formed of unitary construction of molded plastic with at least one of the inner tubular wall and the outer tubular wall
   a measuring electrode disposed in the axial bore of the inner wall and having an tip extending beyond the distal end of the housing to be exposed to a target fluid;
   a reference electrode disposed within the cavity of the housing, submerged in the reference electrolyte; and
   a junction plug comprising a porous material, the junction plug disposed in the distal end of the housing such that a distal surface of the plug is configured to contact the target fluid and a proximal surface of the junction plug is disposed adjacent to the cross member of the housing such that electrochemical communication between the target fluid and the reference electrolyte must pass through the aperture of the cross member.

2. An electrochemical sensor as defined in claim 1, wherein the housing is formed of unitary construction of molded plastic, including the outer wall, the inner wall and the cross member.

3. An electrochemical sensor as defined in claim 1, wherein the cross member defines only a single aperture to enable electrochemical communication between the target fluid and the reference electrolyte.

4. An electrochemical sensor as defined in claim 3, wherein the cross member covers between about 50 percent to 95 percent of the proximal surface of the junction plug.

5. An electrochemical sensor as defined in claim 1, wherein the cross member includes a stepped portion disposed about the axial bore to receive an o-ring disposed about the measuring electrode to inhibit target fluid from the axial bore.

6. An electrochemical sensor as defined in claim 1, wherein the cross member is integrally formed with the inner tubular wall, extending between the axial bore of the inner wall and the outer wall.

7. An electrochemical sensor as defined in claim 1, further comprising an upper seal positioned proximate to the proximal end of the housing, the upper seal configured to engage the inner wall and the outer wall to define an upper boundary of the cavity within the housing.

8. An electrochemical sensor as defined in claim 1, wherein the outer wall includes an inwardly facing flange disposed about a distal opening of the outer wall, the flange sized such that the junction plug can be securely seated in place proximate to the distal opening to directly contact the target fluid.

9. An electrochemical sensor as defined in claim 8, wherein an o-ring is disposed about the junction plug to engage the outer wall to provide a secure seal.

10. An electrochemical sensor as defined in claim 1, further comprising a cap disposed on the proximal end of the housing.

11. An electrochemical sensor as defined in claim 1, further comprising an upper seal positioned proximate to the proximal end of the housing, the upper seal configured to engage the inner wall and the outer wall to define an upper boundary of the cavity within the housing.

12. An electrochemical sensor, comprising:
   an elongated housing defining a longitudinal axis, the housing having a proximal end and a distal end configured to be exposed to a target fluid, the housing further defining a cavity substantially filled with a gelled or liquid reference electrolyte, the housing having
      an outer member formed of unitary construction of molded plastic, the outer member including an outer tubular wall axially aligned with the longitudinal axis of the housing, the outer member impermeable to the reference electrolyte and the target fluid,
      an inner member formed of unitary construction of molded plastic having an inner tubular wall and a cross member disposed at a distal end of the inner tubular wall, the inner member disposed within the outer member and impermeable to the reference electrolyte and the target fluid, the inner tubular wall axially aligned with the longitudinal axis of the housing, the inner wall defining an axial bore, and the cross member extending between the outer wall and the inner wall proximate the distal end of the housing, the cross member including a planar portion defining an aperture to enable electrochemical communication between the target fluid and the reference electrolyte within the cavity, wherein the cavity is bounded by the outer wall, the inner wall and the cross member;
   the cross member of the housing is formed of unitary construction of molded plastic with at least one of the inner tubular wall and the outer tubular wall
   a measuring electrode disposed in the axial bore of the inner wall and having an tip extending beyond the distal end of the housing to be exposed to a target fluid;
   a reference electrode disposed within the cavity of the housing, submerged in the reference electrolyte; and
   a junction plug comprising a porous material, the junction plug disposed in the distal end of the housing such that a distal surface of the plug is configured to contact the target fluid and a proximal surface of the junction plug is disposed adjacent to the cross member of the housing such that electrochemical communication between the target fluid and the reference electrolyte must pass through the aperture of the cross member.

13. An electrochemical sensor as defined in claim 12, wherein the cross member defines only a single aperture to enable electrochemical communication between the target fluid and the reference electrolyte.

14. An electrochemical sensor as defined in claim 13, wherein the cross member covers between about 50 percent to 95 percent of the proximal surface of the junction plug.

15. An electrochemical sensor as defined in claim 12, wherein the cross member includes a stepped portion disposed about the axial bore to receive an o-ring disposed about the measuring electrode to inhibit target fluid from the axial bore.

16. A method of manufacturing an electrochemical sensor, comprising:
   providing an elongated housing defining a longitudinal axis, the housing having a proximal end and a distal end configured to be exposed to a target fluid, the housing further defining a cavity the housing having
      an outer tubular wall formed of molded plastic, axially aligned with the longitudinal axis of the housing, the outer wall impermeable to the reference electrolyte and the target fluid,
      an inner tubular wall formed of molded plastic, disposed within the outer wall, and axially aligned with the longitudinal axis of the housing, the inner wall impermeable to the reference electrolyte and the target fluid, the inner wall defining an axial bore, and
      a cross member extending between the outer wall and the inner wall proximate the distal end of the housing, the cross member including a planar portion defining an aperture to enable electrochemical communication between the target fluid and the reference electrolyte within the cavity, wherein the cavity is bounded by the outer wall, the inner wall and the cross member;
   the cross member of the housing is formed of unitary construction of molded plastic with at least one of the inner tubular wall and the outer tubular wall
   providing a measuring electrode sized to be disposed in the axial bore of the inner wall and having an tip extending beyond the distal end of the housing to be exposed to a target fluid;
   providing a junction plug a comprising a porous material, the junction plug sized to be disposed in the distal end of the housing such that a distal surface of the plug is configured to contact the target fluid and a proximal surface of the junction plug is disposed adjacent to the cross member of the housing such that electrochemical communication between the target fluid and the reference electrolyte must pass through the aperture of the cross member;
   inserting the junction plug onto the measuring electrode, and then placing the combination of the junction plug and the measuring electrode into the housing;
   filling the cavity of the housing with a gelled or liquid reference electrolyte; and
   inserting a reference electrode into the cavity.

17. A method as defined in claim 16, further comprising placing an upper seal within the housing positioned proximate to the proximal end of the housing to engage the inner wall and the outer wall to define an upper boundary of the cavity within the housing.

18. A method as defined in claim 17, further comprising placing a cap on the proximal end of the housing.

* * * * *